United States Patent [19]

Ono

[11] Patent Number: 5,705,656
[45] Date of Patent: Jan. 6, 1998

[54] N-ALKYLATION METHOD OF PYRAZOLE

[75] Inventor: Yoshio Ono, Kawasaki, Japan

[73] Assignee: Nissan Chemical Industries Ltd., Tokyo, Japan

[21] Appl. No.: 662,251

[22] Filed: Jun. 14, 1996

[30] Foreign Application Priority Data

Jun. 21, 1995 [JP] Japan ................................. 7-154682

[51] Int. Cl.$^6$ ................................. C07D 231/12
[52] U.S. Cl. ................................. 548/373.1; 548/377.1
[58] Field of Search ................................. 548/373.1, 377.1

[56] References Cited

U.S. PATENT DOCUMENTS

| | | | |
|---|---|---|---|
| 3,962,364 | 6/1976 | Young | 260/671 |
| 4,358,395 | 11/1982 | Haag et al. | 252/411 |
| 4,861,929 | 8/1989 | Miyake et al. | 570/209 |
| 5,453,534 | 9/1995 | Eller | 560/187 |
| 5,468,871 | 11/1995 | Ebel et al. | 548/373.1 |

FOREIGN PATENT DOCUMENTS

| | | |
|---|---|---|
| 0 628 563 | 12/1994 | European Pat. Off. . |
| 1 603 793 | 5/1971 | France . |

OTHER PUBLICATIONS

Chemical Abstracts, AN–23466t, vol. 114, No. 3, 1991, S. Prasad, et al., "Mechanism of Aniline Alkylation with Methanol Over Aluminophosphate (ALPO4–5)" & J. Mol. Catal, vol. 62, No. 2, 1990.

*Primary Examiner*—Joseph McKane
*Attorney, Agent, or Firm*—Oblon, Spivak, McClelland, Maier & Neustadt, P.C.

[57] ABSTRACT

An N-alkylation method of pyrazole in which (III) is produced from (I) and (II), which is characterized by using a crystalline aluminosilicate or a crystalline aluminophosphate as a catalyst:

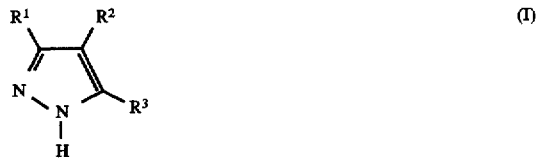

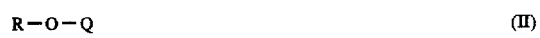

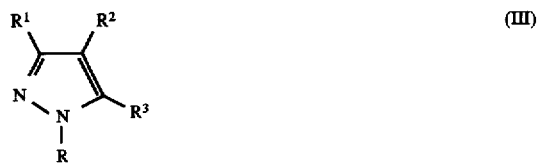

wherein each of $R^1$, $R^2$ and $R^3$ represents hydrogen, alkyl, alkenyl or phenyl, R represents alkyl and Q represents hydrogen, alkyl or COOR. This is an industrially markedly useful method, because (III) can be obtained with a high yield under mild reaction conditions, and by-products including salts are not at all formed.

22 Claims, No Drawings

N-ALKYLATION METHOD OF PYRAZOLE

FIELD OF THE INVENTION

This invention relates to a process for the production of an N-alkylpyrazole derivative which is useful as starting materials or intermediates for various fine chemicals such as agricultural chemicals, pharmaceutical drugs and the like.

PRIOR ART

Various heterocyclic compounds have been used as starting materials and intermediates of various fine chemicals, such as agricultural chemicals, pharmaceutical drugs, dyestuffs, photo-sensitive materials and the like. N-Substituted pyrazole derivatives can be included as a typical example of the heterocyclic compounds.

In general, a method in which an N-mono-substituted hydrazine is allowed to react with a 1,3-dicarbonyl compound is known as a conventional method for the production of an N-substituted pyrazole derivative. This method is markedly simple and useful at a laboratory level, but most of the N-mono-substituted hydrazines are generally expensive, so that another method is selected as an industrial method in most cases in which an N-non-substituted pyrazole derivative is firstly obtained using inexpensive hydrazine and then its corresponding N-alkylpyrazole derivative is obtained through an N-alkylation reaction.

For the production of an N-alkylpyrazole derivative from an N-nonsubstituted pyrazole derivative, a general synthetic method has been reported in which the starting material is allowed to react with a highly reactive alkylating agent, typically with an alkyl halide, in the presence of a theoretical amount of a base, as disclosed for example in:

(1) European Patent Publication No. 454,307, (2) *Journal of Organic Chemistry* (*J. Org. Chem.*), vol.49, no.24, p.4687, 1984, and (3) *Journal of Medicinal Chemistry* (*J. Med. Chem.*), vol.27, no.4, p.539, 1984.

In recent years, methods in which an alcohol is used have been reported, such as (4) a method reported in *Chemistry Letter* (*Chem. Lett.*), p.575, 1992, in which a complex catalyst of the group VIII is used, and (5) a method disclosed in European Patent Publication No. 628,563 in which a γ-alumina and/or silica catalyst is used.

In the case of the methods (1) to (3) above, all of them require a base or a condensing agent in a theoretical amount or more, so that a large amount of salts and the like are by-produced which cause industrial troubles in many cases.

The methods in which an alcohol is used can be regarded as excellent methods, because only water is basically by-produced, but the method (4) above in which a complex catalyst of the group VIII is used has a problem in that the catalyst to be used is not always inexpensive industrially. The other method (5) in which silica and/or alumina alone or together with phosphoric acid is used as a catalyst requires an elevated reaction temperature of 400° C. or more in most cases and has a problem in that the reproducibility of catalyst activity can hardly be obtained due to amorphous substances, such as silica and/or alumina. In addition, the use of phosphoric acid-added catalyst may result in scattering of phosphoric acid when used for a prolonged period of time.

In consequence, great concern has been directed toward the development of a more excellent method for the production of an N-alkylpyrazole derivative, which is inexpensive, safe, industrially easily accessible and applicable to the synthesis of N-alkylpyrazole derivatives having various substituent groups using N-nonsubstituted pyrazole derivative as a starting material.

Disclosure of the Invention

With the aim of overcoming the aforementioned problems, the inventors have conducted intensive studies and accomplished the present invention as a result of the effort.

The gist of the present invention resides in a method for producing an N-alkylpyrazole derivative represented by the formula (III):

(III)

wherein each of $R^1$, $R^2$ and $R^3$ independently represents a hydrogen atom, a $C_{1-20}$ alkyl group which may optionally have an alicyclic structure in its structure or may be substituted with a phenyl group, a $C_{2-20}$ alkenyl group which may optionally have an alicyclic structure in its structure or may be substituted with a phenyl group, or a phenyl group, from a pyrazole derivative represented by the formula (I):

(I)

wherein each of $R^1$, $R^2$ and $R^3$ is as defined in the formula (III) above, and an alcohol or a derivative thereof represented by the formula (II):

R—O—Q  (II)

wherein R represents a $C_{1-20}$ alkyl group and Q represents a hydrogen atom, a $C_{1-20}$ alkyl group or a COOR group, which method is characterized in that N-alkylation of said pyrazole is carried out using a crystalline aluminosilicate or a crystalline aluminophosphate as a catalyst. This method is referred to as "the method of the present invention" hereinafter.

The following describes the pyrazole derivative represented by formula (I) and the alcohol or alcohol derivative represented by formula (II) to be used in the method of the present invention.

Examples of the groups $R^1$, $R^2$ and $R^3$ include hydrogen atom, methyl group, ethyl group, n-propyl group, iso-propyl group, n-butyl group, iso-butyl group, sec-butyl group, tert-butyl group, n-amyl group, iso-amyl group, neopentyl group, n-hexyl group, n-heptyl group, 2-ethylhexyl group, n-octyl group, n-nonyl group, n-decyl group, n-dodecyl group, n-hexadecyl group, n-octadecyl group, cyclopropyl group, cyclobutyl group, cyclopentyl group, cyclohexyl group, cyclooctyl group, cyclopropylmethyl group, cyclobutylmethyl group, cyclopentylmethyl group, cyclohexylmethyl group, benzyl group, 1-phenethyl group, 2-phenethyl group, 3-phenylpropyl group, vinyl group, 2-propenyl group, allyl group, methallyl group, crotyl group, 3-butenyl group, 3-hexenyl group, cinnamyl group and the like.

Examples of the group R include methyl group, ethyl group, n-propyl group, iso-propyl group, n-butyl group, iso-butyl group, sec-butyl group, tert-butyl group, n-amyl group, iso-amyl group, neopentyl group, n-hexyl group, n-heptyl group, 2-ethylhexyl group, n-octyl group, n-nonyl group, n-decyl group, n-dodecyl group, n-hexadecyl group, n-octadecyl group and the like.

Examples of the group Q include hydrogen atom, COOCH$_3$ and the like.

Next, the catalyst is described below.

Examples of the catalyst include a crystalline aluminosilicate and a crystalline aluminophosphate, of which a crystalline aluminosilicate is preferred.

Examples of the crystalline aluminosilicate include aluminosilicates having various structures, such as faujasite (X and Y), EMT, mordenite, beta, L and ZSM-5 (zeolites in a narrow sense) and aluminosilicates whose skeletons are isomorphously substituted with ions such as of boron, gallium and the like.

Examples of the crystalline aluminophosphate include aluminophosphate (AlPO$_4$-n, n=5, 11, 36 and the like), silicoaluminophosphate (SAPO-n, n=5, 11, 36 and the like) and aluminophosphate and silicoaluminophosphate isomorphously substituted with metal ions such as of Mn, Zn and the like (MAPO-n, ZAPO-n, MAPSO-n, ZAPSO-n, n=5, 11, 36 and the like).

Of these, crystalline substances having a pore size of 0.7 to 1.0 nm are particularly preferred as the catalyst of the inventive reaction, which include faujasite, EMT, beta, SAPO-5, MAPO-5, MAPO-36 and the like.

In addition, these substances show particularly high catalytic activity when they have a solid acidity (cation). In the case of zeolite in a narrow sense and silicoaluminophosphate, this can be achieved by introducing protons into the pores as the cations. This can also be achieved by introducing divalent cations, such as Mg$^{2+}$, Cu$^{2+}$ and the like, or trivalent ions, such as La$^{3+}$ and the like, into pores.

In the reaction, various reaction modes can be selected, such as a flow system reaction mode in which a starting material is vaporized and allowed to undergo the reaction in a packed bed reactor with the aforementioned catalyst and a batch reaction mode in which a catalyst and a starting material are allowed to react with each other by mixing them in an autoclave or the like reactor, but it is desirable to carry out the reaction in a gas phase flow system mode from the viewpoint of workability, productivity and the like.

Amounts of the alcohol or alcohol derivative of formula (II) to be used in the reaction can be selected at will depending on the purpose of the reaction, but it is generally desirable to use the alcohol or the derivative thereof of formula (II) in an amount of generally from 0.01 to 50 moles, preferably from 0.1 to 20 moles, more preferably from 0.5 to 10 moles, per mole of the pyrazole derivative of formula (I).

In the case of the gas phase flow system reaction mode, the reaction is carried out by simultaneously heating and vaporizing both the pyrazole derivative of formula (I) and the alcohol or alcohol derivative of formula (II) and then continuously feeding them into a reactor.

The reaction temperature is generally from 150° to 400° C., preferably from 200° to 350° C.

The reaction can be carried out under any pressure within the range of generally from 1 to 10,000 kPa as the total of partial pressures of the aforementioned starting materials, but preferably within the range of from 5 to 1,000 kPa in view of workability, productivity, safety and the like.

Though the reaction can be carried out by vaporizing only the aforementioned starting materials, it is desirable to use an inert gas, such as nitrogen, argon or the like, or other gas inert to the reaction as a carrier gas. In that case, it is desirable to carry out the reaction under a pressure within the range of generally from 10 to 10,000 kPa, preferably from 50 to 5,000 kPa, as the total pressure in the reaction system.

With regard to the reaction time in the case of the gas phase flow system reaction mode, suitable space velocity S/V is selected depending on the reactivity of the substrate to be used, activity of the catalyst and the like, which is generally from 3×10 to 3×10$^5$ h$^{-1}$ but preferably from 6×10 to 2×10$^5$ h$^{-1}$ when yield, productivity and the like are taken into consideration.

After completion of the reaction, a pure N-alkylpyrazole derivative can be easily obtained by a post-treatment, e.g. by evaporating the by-produced water and unreacted alcohol or derivative thereof from the reaction solution in the reactor or by concentrating the reaction solution and then subjecting it to fractional distillation. When the alcohol or a derivative thereof of formula (II) is used in an amount of 1 mole per mole of the pyrazole derivative of formula (I) and the reaction ratio is 100% or close to it, a high purity N-alkylpyrazole derivative having no practical problems can be obtained by simply evaporating water or by separating it using a liquid separation operation from the reaction solution in the reactor.

EXAMPLES

Examples of the present invention are given below by way of illustration and not by way of limitation.

In all cases of the following Examples, amounts of each substance in the reaction product were accurately measured by a gas chromatographic internal standard determination method using a calibration curve prepared in advance with pure substances separately synthesized and isolated and an internal standard compound.

Example 1

Synthesis of 1-methylpyrazole

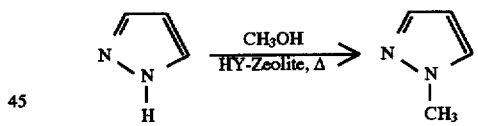

A normal pressure flow system reaction tube made of quartz was packed with 0.72 g of HY-zeolite catalyst, a kind of acidic faujasite and heated at 300° C., and pyrazole and methanol were vaporized and continuously fed with respective partial pressures of 16.7 kPa and 33.3 kPa together with nitrogen under a total pressure of 1 atmosphere and at a space velocity S/V of 7.5×10$^2$ h$^{-1}$. The gas obtained from the reactor was cooled and condensed to form a crude reaction solution, which was analysed with a gas chromatography apparatus. As a result of the analysis, conversion ratio of the starting pyrazole was found to be 100% and N-methylpyrazole was obtained with a yield of 100% based on the supplied pyrazole.

Examples 2 to 7

In accordance with the procedure of Example 1, the reaction was carried out except that the S/V values and reaction temperature were changed. The results are shown in Table 1 below.

TABLE 1

N-Methylation reaction of pyrazole

| Example No. | S/V ($h^{-1}$) | Reaction temp. (°C.) | Pyrazole conversion (%) | Methylpyrazole yield (%) |
|---|---|---|---|---|
| 2 | $7.5 \times 10^2$ | 270 | 100 | 100 |
| 3 | $7.5 \times 10^2$ | 240 | 100 | 98 |
| 4 | $1.4 \times 10^3$ | 300 | 100 | 100 |
| 5 | $1.4 \times 10^3$ | 270 | 100 | 99 |
| 6 | $2.8 \times 10^3$ | 300 | 100 | 99 |
| 7 | $2.8 \times 10^3$ | 270 | 99 | 97 |
| 8 | $2.8 \times 10^3$ | 240 | 83 | 77 |

Example 9

Synthesis of 1,4-dimethylpyrazole (DP)

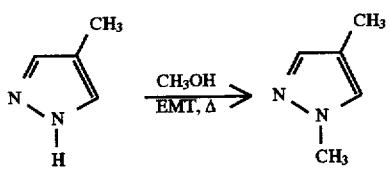

In accordance with the procedure of Example 1, a normal pressure flow system reaction tube made of quartz was packed with 1.0 g of H-EMT catalyst and heated at 300° C., and 4-methylpyrazole (MP) and methanol were vaporized and continuously fed with respective partial pressures of 8.2 kPa and 42.5 kPa together with nitrogen under a total pressure of 1 atmosphere and at an S/V of $7.5 \times 10^2$ $h^{-1}$. The gas obtained from the reactor was cooled and condensed to form a crude reaction solution, which was analysed with a gas chromatography apparatus. As a result of the analysis, conversion ratio of the starting material MP was found to be 100% and 1,4-dimethylpyrazole (DP) was obtained with a yield of 100% based on the supplied MP.

Example 10

Synthesis of 1,4-dimethylpyrazole (DP)

In accordance with the procedure of Example 9, a normal pressure flow system reaction tube made of quartz was packed with 1.0 g of HY-zeolite catalyst, a kind of acidic faujasite and heated at 300° C., and 4-methylpyrazole (MP) and methanol were vaporized and continuously fed with respective partial pressures of 8.2 kPa and 42.5 kPa together with nitrogen under a total pressure of 1 atmosphere and at an S/V of $7.5 \times 10^2$ $h^{-1}$. The gas obtained from the reactor was cooled and condensed to form a crude reaction solution, which was analysed with a gas chromatography apparatus. As a result of the analysis, conversion ratio of the starting material MP was found to be 100% and 1,4-dimethylpyrazole (DP) was obtained with a yield of 100% based on the supplied MP.

Examples 11 to 14

In accordance with the procedure of the aforementioned Example, the reaction was carried out except that partial pressures of MP and methanol, S/V values and reaction temperature were changed. The results are shown in Table 2 below.

TABLE 2

Synthesis of 1,4-dimethylpyrazole (DP) by N-methylation of 4-methylpyrazole (MP)

| Example No. | Partial pressure (kPa) MP | Partial pressure (kPa) CH$_3$OH | S/V ($h^{-1}$) | Reaction temperature (°C.) | MP conversion ratio (%) | DP yield (%) |
|---|---|---|---|---|---|---|
| 11 | 16.9 | 33.7 | $7.5 \times 10^2$ | 270 | 100 | 99 |
| 12 | 25.3 | 25.3 | $5.8 \times 10^2$ | 300 | 100 | 97 |
| 13 | 25.3 | 25.3 | $9.3 \times 10^2$ | 270 | 99 | 99 |
| 14 | 25.3 | 25.3 | $7.5 \times 10^2$ | 300 | 100 | 100 |

Comparative Example

Synthesis of 1,4-dimethylpyrazole (DP)

In accordance with the procedure of Example 9, a normal pressure flow system reaction tube made of quartz was packed with 1.0 g of a phosphoric acid/silica (phosphoric acid 22%) catalyst and heated at 270° C., and 4-methylpyrazole (MP) and methanol were vaporized and continuously fed with respective partial pressures of 25.3 kPa and 25.3 kPa together with nitrogen under a total pressure of 1 atmosphere and at an S/V of $5.8 \times 10^2$ $h^{-1}$. The gas obtained from the reactor was cooled and condensed to form a crude reaction solution, which was analysed with a gas chromatography apparatus. As a result of the analysis, conversion ratio of the starting material MP was found to be 79%, and 1,4-dimethylpyrazole (DP) was obtained with a yield of 68% based on the supplied MP.

Advantages of the Invention

According to the method of the present invention, N-alkylpyrazole derivatives of interest can be obtained with a high yield from industrially available and inexpensive N-nonsubstituted pyrazole derivatives under mild reaction conditions. In addition, the method of the present invention is an industrially markedly useful method, because pure N-alkylpyrazole derivatives can be obtained easily by merely separating water from the reaction solution in essence due to no generation of by-products including salts which sometimes cause troubles in the conventional methods.

I claim:

1. A method for producing an N-alkylpyrazole compound represented by the formula (III):

wherein each of $R^1$, $R^2$ and $R^3$ is independently selected from the group consisting of a hydrogen atom, a $C_{1-20}$ alkyl group, a $C_{2-20}$ alkenyl group, a cyclopropyl group, a cyclobutyl group, a cyclopentyl group, a cyclohexyl group, a cyclooctyl group, a cyclopropylmethyl group, a cyclobutylmethyl group, a cyclopentylmethyl group, a cyclohexylmethyl group, a benzyl group, a 1-phenethyl group, a 2-phenethyl group, a 3-phenylpropyl group, a cinnamyl group, and a phenyl group, from a pyrazole compound represented by the formula (I):

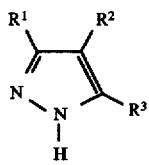 (I)

wherein each of $R^1$, $R^2$ and $R^3$ is as defined in the formula (III) above, and an alcoholic compound represented by the formula (II):

 (II)

wherein R represents a $C_{1-20}$ alkyl group and Q represents a hydrogen atom, a $C_{1-20}$ alkyl group or a COOR group, wherein N-alkylation of said pyrazole compound is carried out using a crystalline aluminosilicate or a crystalline aluminophosphate as a catalyst.

2. The method according to claim 1 wherein the catalyst has a pore size of 0.7 to 1.0 nm.

3. The method according to claim 1 wherein the catalyst has a solid acidity.

4. The method according to claim 1 wherein the catalyst has a proton as the cation.

5. The method according to claim 1 wherein the catalyst has a divalent or trivalent metal ion as the cation.

6. The method according to claim 1 wherein the catalyst is a crystalline aluminosilicate.

7. The method according to claim 6 wherein the crystalline aluminosilicate has a pore size of 0.7 to 1.0 nm.

8. The method according to claim 7 wherein the crystalline aluminosilicate contains a proton as the cation.

9. The method according to claim 8 wherein the crystalline aluminosilicate has a crystal structure of faujasite.

10. The method according to claim 8 wherein the crystalline aluminosilicate has a crystal structure of EMT.

11. The method according to claim 8 wherein the crystalline aluminosilicate has a crystal structure of beta.

12. The method according to claim 6 wherein the catalyst has a divalent or trivalent metal ion as the cation.

13. The method according to claim 12 wherein the crystalline aluminosilicate has a crystal structure of faujasite.

14. The method according to claim 12 wherein the crystalline aluminosilicate has a crystal structure of EMT.

15. The method according to claim 1 wherein the catalyst is a crystalline aluminophosphate.

16. The method according to claim 1 wherein each of $R^1$, $R^2$ and $R^3$ independently represents a hydrogen atom, a $C_{1-20}$ alkyl group, a $C_{2-20}$ alkenyl group or a phenyl group.

17. The method according to claim 1 wherein each of $R^1$, $R^2$ and $R^3$ independently represents a hydrogen atom or a methyl group.

18. The method according to claim 1 wherein R represents a $C_{1-4}$ alkyl group.

19. The method according to claim 1 wherein R represents a methyl group.

20. The method according to claim 1 wherein Q represents a hydrogen atom.

21. The method according to claim 20 wherein R represents a $C_{1-4}$ alkyl group and each of $R^1$, $R^2$ and $R^3$ independently represents a hydrogen atom or a methyl group.

22. The method according to claim 20 wherein R represents a methyl group and each of $R^1$, $R^2$ and $R^3$ independently represents a hydrogen atom or a methyl group.

* * * * *